(12) United States Patent
Yamazaki et al.

(10) Patent No.: US 10,124,270 B2
(45) Date of Patent: Nov. 13, 2018

(54) GAS BLOWING VAPORIZING AND DRYING DEVICE

(75) Inventors: Tomoyuki Yamazaki, Kyoto (JP);
Przemyslaw Stasica, Stevenage (GB);
Bob Boughtflower, Ware (GB)

(73) Assignee: SHIMADZU CORPORATION,
Kyoto-shi (JP)

( * ) Notice: Subject to any disclaimer, the term of this patent is extended or adjusted under 35 U.S.C. 154(b) by 1040 days.

(21) Appl. No.: 14/234,829

(22) PCT Filed: Jul. 4, 2012

(86) PCT No.: PCT/JP2012/067070
§ 371 (c)(1),
(2), (4) Date: Apr. 7, 2014

(87) PCT Pub. No.: WO2013/015081
PCT Pub. Date: Jan. 31, 2013

(65) Prior Publication Data
US 2014/0224430 A1  Aug. 14, 2014

(30) Foreign Application Priority Data

Jul. 26, 2011  (JP) ................................ 2011-163097
Jul. 26, 2011  (JP) ................................ 2011-163098

(51) Int. Cl.
*G01N 35/10* (2006.01)
*B01D 1/18* (2006.01)
(Continued)

(52) U.S. Cl.
CPC ............... *B01D 1/18* (2013.01); *B01D 1/14* (2013.01); *B01D 15/24* (2013.01); *G01N 30/84* (2013.01);
(Continued)

(58) Field of Classification Search
CPC . G01N 35/10; G01N 35/1009; G01N 35/1034
(Continued)

(56) References Cited

U.S. PATENT DOCUMENTS 5,433,120 A * 7/1995 Boyd .................... G01N 1/2035
                                                     73/863.71
5,945,070 A * 8/1999 Kath .................... B01J 19/0046
                                                     422/535
(Continued)

FOREIGN PATENT DOCUMENTS

GB       2465955 A      6/2010
JP       60-11054 A     1/1985
(Continued)

OTHER PUBLICATIONS

Japanese Office Action dated Apr. 21, 2015 in Japanese Patent Application No. 2013-525643.
Communication dated Jun. 11, 2018 issued by the Intellectual Property Office of the United Kingdom in counterpart application No. 1402651.2.

*Primary Examiner* — Jill A Warden
*Assistant Examiner* — Dwayne K Handy
(74) *Attorney, Agent, or Firm* — Sughrue Mion, PLLC

(57) ABSTRACT

Provided is a gas-blowing vaporizing and drying device for blowing gas at a solution containing a target component, and thus nebulizing the solution to promote vaporization of the solvent while dropping the solution into the collection container, in which contamination does not occur even if different solutes are successively powderized. In the gas-blowing vaporizing and drying device according to the present invention, a cap 20 to be fitted to the upper opening of a collection container body 19 includes: a solution-introducing tube 20A for introducing a solution supplied from a passage 14, into a collection container 21; a gas-introducing tube 20B for introducing a gas supplied from a passage 22, into the collection container 21; and an exhaust (Continued)

port 20C. Further, the exhaust port 20C includes a filter 20D for preventing the powderized solute from passing therethrough.

9 Claims, 7 Drawing Sheets

(51) Int. Cl.
  *B01D 1/14*    (2006.01)
  *B01D 15/24*   (2006.01)
  *G01N 30/84*   (2006.01)
(52) U.S. Cl.
  CPC ..... *G01N 35/1004* (2013.01); *G01N 35/1079* (2013.01)
(58) Field of Classification Search
  USPC .......................... 422/501, 509, 511, 512, 522
  See application file for complete search history.

(56) References Cited

U.S. PATENT DOCUMENTS

| | | |
|---|---|---|
| 2007/0193871 A1 | 8/2007 | Wiseman et al. |
| 2010/0300627 A1 | 12/2010 | Kono et al. |

FOREIGN PATENT DOCUMENTS

| | | |
|---|---|---|
| JP | 2-122260 A | 5/1990 |
| JP | 2003-149217 A | 5/2003 |
| JP | 2003-215137 A | 7/2003 |
| JP | 54-58681 | 4/2014 |
| WO | 2009/044425 A1 | 4/2009 |
| WO | 2009/044426 A1 | 4/2009 |
| WO | 2009/044427 A1 | 4/2009 |
| WO | 2009/044428 A1 | 4/2009 |

* cited by examiner

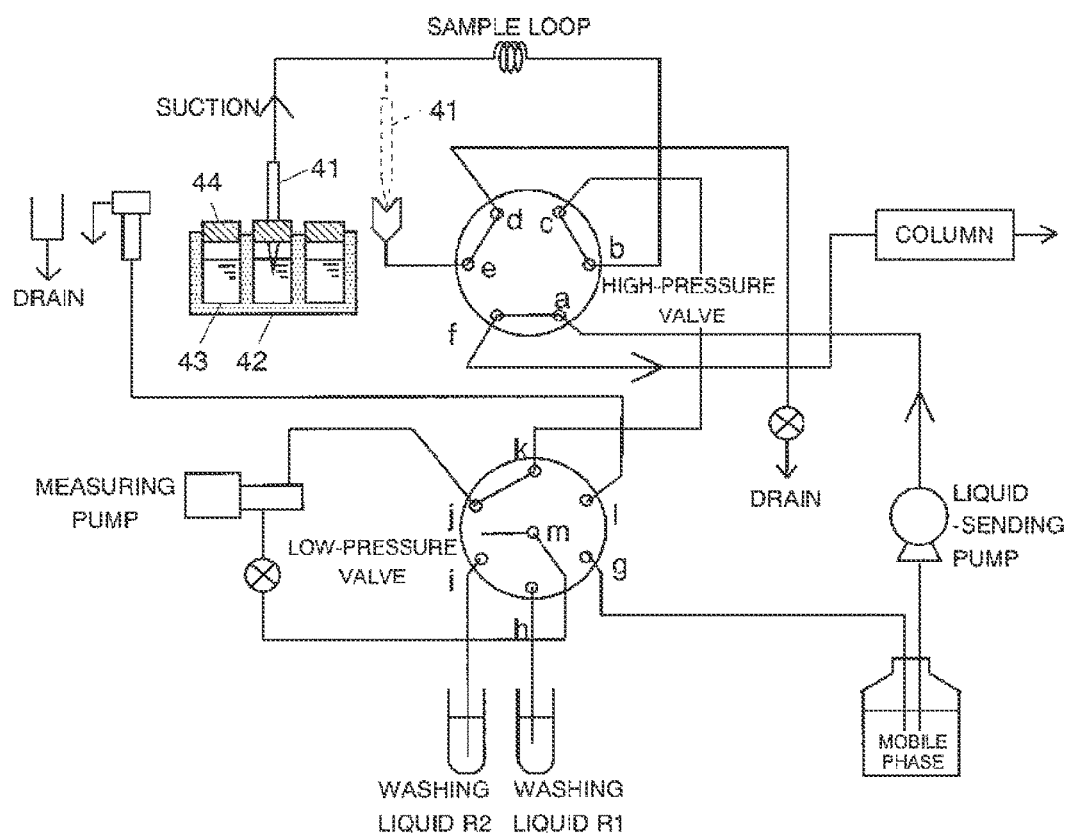

GAS BLOWING VAPORIZING AND DRYING DEVICE

CROSS REFERENCE TO RELATED APPLICATIONS

This application is a National Stage of International Application No. PCT/JP2012/067070 filed Jul. 4, 2012, claiming priority based on Japanese Patent Application Nos. 2011-163097 and 2011-163098 filed Jul. 26, 2011, the contents of all of which are incorporated herein by reference in their entirety.

TECHNICAL FIELD

The present invention relates to a gas-blowing vaporizing and drying device for nebulizing a solution containing a target component to promote vaporization of the solvent by blowing gas at the solution while dropping the solution into a collection container. The present gas-blowing vaporizing and drying device can be suitably used in a preparative separation-purification system for purifying and collecting one or a plurality of components contained in a solution and separated by using a liquid chromatograph.

BACKGROUND ART

Preparative separation-purification systems using liquid chromatographs are used in pharmaceutical or similar fields for the purpose of collecting samples for storing various compounds obtained through chemical synthesis in the form of a library, or for analyzing the various compounds in detail. Systems described in Patent Document 1 and Patent Document 2 are known as some of such preparative separation-purification systems.

In such systems, target components (compounds) in a sample solution are temporally separated by a liquid chromatograph. Then, the separated target components are introduced into respective trap columns and temporarily captured therein. Subsequently, a solvent is flown through each trap column to elute the captured component from the trap column, whereby the solution containing the target component at a high concentration is collected in a container. Then, each collected solution is subjected to a vaporizing and drying process to remove the solvent and collect the target component in the form of solid.

The vaporizing and drying process is normally performed according to, for example, a method of heating or centrifuging the collected solution. In this case, it takes several hours or even days to perform this method. In order to find effective medicinal compounds from many synthetic compounds, especially in pharmaceutical fields, various improvements in efficiency have been attempted. For example, an analysis time is shortened by increasing the analysis speed of analytical instruments, or by optimizing analytical methods. However, the vaporizing and drying process is the longest process among all processes, and hence it is critical to shorten this process.

A method for solving this problem is disclosed in Patent Documents 3 to 6. The method involves dropping a solution containing a target component into a collection container while blowing air, nitrogen, or another kind of gas at the drops of the solution, and thus nebulizing the solution to assist vaporization by heating of the solvent.

A normal procedure of the vaporizing and drying process according to the method of Patent Documents 3 to 6 (hereinafter, referred to as "gas-blowing vaporizing and drying process") is described with reference to FIGS. 9A-9D. A preparative separation-purification system is provided with a needle 50 having a triple-tube structure including a solution-introducing tube 50A, a gas-introducing tube 50B that encloses the solution-introducing tube 50A, and a washing-liquid-introducing tube 50C that encloses the gas-introducing tube 50B as illustrated in FIG. 9C. The inner of the introducing tubes 50A, 50B and 50C protrudes from the outer one. A collection container 53 housed in a temperature regulated block 54 is placed below the needle 50. The collection container 53 includes a collection container body 51 and a cap 52 to be fitted to the upper opening of the collection container body 51. The cap 52 includes two septa 52A and a doughnut-shaped cushion 52B sandwiched between the two septa 52A.

In this process, the needle 50 is moved downward, and passes through the central hole of the cushion 52B while penetrating through the septa 52A, until its tip come into the collection container 53. Along with this downward movement of the needle 50, an exhaust duct 55 is also moved downward, and is brought into tight contact with the cap 52 by means of the cushion 52B so as to cover the hole that is formed in the cap 52 by the needle 50. Subsequently, a solution and a gas are respectively introduced through the solution-introducing tube 50A and the gas-introducing tube 50B into the collection container 53.

After passing through the solution-introducing tube 50A, the solution is dropped from the tip of the needle 50 inserted into the collection container 53, and simultaneously, gas is ejected from the gas-introducing tube 50B provided outside of the solution-introducing tube 50A. By this gas flow from the gas-introducing tube 50B, the solution being dropped from the solution-introducing tube 50A is sheared into fine droplets (mist) and the droplets attach to the inner wall of the collection container 53. Since the collection container 53 is heated by the temperature regulated block 54 surrounding the container, the solvent in the fine droplets attached to the inner wall vaporizes, so that only the solute remains in the form of powder. The gas introduced into the collection container 53 and the vaporized solvent pass through the gap of the hole that is formed by the needle 50 penetrating through the cap 52, and then pass through the exhaust duct 55, to be discharged to the outside of the collection container 53.

In this gas-blowing vaporizing and drying process, the solute may deposit on the tip of the needle 50. As a result, the gas flow from the gas-introducing tube 50B may be changed, or part of the gas flow may be hindered, so that the shearing efficiency of the dropped solution may be decreased. In such a case, a washing liquid (normally, a solvent that has a strong eluting power and easily vaporizes, such as dichloromethane) is introduced through the washing-liquid-introducing tube 50C, to thereby wash the portion of the gas-introducing tube 50B protruding from the washing-liquid-introducing tube 50C and the portion of the solution-introducing tube 50A protruding from the gas-introducing tube 50B.

BACKGROUND ART DOCUMENT

Patent Document

[Patent Document 1] JP-A 2-122260
[Patent Document 2] JP-A 2003-149217
[Patent Document 3] WO 2009/044425
[Patent Document 4] WO 2009/044426
[Patent Document 5] WO 2009/044427
[Patent Document 6] WO 2009/044428

DISCLOSURE OF THE INVENTION

Problem to be Solved by the Invention

The gas-blowing vaporizing and drying process illustrated in FIGS. 9A-9D has the following problem.

The powderized solute is scattered within the collection container by the gas ejected from the gas-introducing tube 50B. If the scattered powder attaches to the outer surface of the washing-liquid-introducing tube 50C, the attached powder cannot be washed by the washing liquid fed from the washing-liquid-introducing tube 50C. Hence, in the case where a different solute is powderized in the next collection container with the powder attached to the outer surface of the washing-liquid-introducing tube 50C, carry-over contamination occurs.

The present invention has been developed to solve the above-mentioned problem, and its objective is to provide a gas-blowing vaporizing and drying device in which contamination does not occur when different solutes are successively powderized.

Means for Solving the Problem

The present invention aimed at solving the above-mentioned problem provides a gas-blowing vaporizing and drying device including a collection container for collecting a target component, the gas-blowing vaporizing and drying device being for blowing gas at a solution containing a target component and thus nebulizing the solution to promote vaporization of the solvent while dropping the solution into the collection container. The collection container includes: a collection container body; and a lid including: a solution-introducing tube for introducing the solution, supplied from a solution passage through which the solution flows, into the collection container; a gas-introducing tube for introducing the gas, supplied from a gas passage through which the gas flows, into the collection container; and an exhaust port.

In the gas-blowing vaporizing and drying device according to the present invention, each collection container includes the solution-introducing tube and the gas-introducing tube. Hence, even if the solution-introducing tube and the gas-introducing tube are contaminated by powderization, the contamination does not influence the next collection container. Accordingly, in the gas-blowing vaporizing and drying device according to the present invention, such contamination as described above does not occur.

It is desirable to provide a filter to the exhaust port. As a result, because a new filter is used each time the collection containers are changed from one to another, the filter provided downstream of an exhaust duct is not clogged, and the device can continuously run for a long time.

In the gas-blowing vaporizing and drying device according to the present invention, it is preferable in terms of a configuration to adopt a form in which a connection unit is fitted to the lid at the time of performing a gas-blowing vaporizing and drying process, the connection unit including: a solution connection tube that is provided at an outlet end of the solution passage and is to be fitted to an inlet end of the solution-introducing tube; a gas connection tube that is provided at an outlet end of the gas passage and is to be fitted to an inlet end of the gas-introducing tube; and an exhaust duct.

The gas-introducing tube may be provided on an axis different from that of the solution-introducing tube, but it is desirable that the gas-introducing tube be provided on the same axis as that of the solution-introducing tube and that a double-tube structure be adopted in which the solution-introducing tube is an inner tube while the gas-introducing tube is an outer tube. This is because the shearing efficiency of the solution can be more enhanced.

It is desirable that the gas-blowing vaporizing and drying device according to the present invention further include gas-introducing tube washing means for feeding a washing liquid to the gas-introducing tube through the gas passage. As a result, the gas-introducing tube can be washed while the connection state between the gas passage and the gas-introducing tube is maintained.

It is desirable that the gas-blowing vaporizing and drying device according to the present invention further include: a housing unit for housing the collection container, the housing unit being fixed at a predetermined position; and fixing means for fixing the collection container to the housing unit, the fixing means being provided to any one or both of the collection container and the housing unit. As a result, it is possible to prevent the collection container from falling to be damaged and prevent the powderized target component from spilling.

In a form that can be adopted for the fixing means, an outer circumferential surface of the lid and an inner circumferential surface of the housing unit include a screw thread and a thread groove corresponding to each other. Further, it is desirable that an outer circumferential surface of the collection container body and an inner circumferential surface of the lid include a screw thread and a thread groove corresponding to each other and that axes and turn directions of a screw pair for fixing the lid and the collection container body and a screw pair for fixing the lid and the housing unit be the same as each other. As a result, when the collection container body is housed in the housing unit and the lid is fitted to the collection container body, the lid is fixed to the housing unit at the same time.

Effects of the Invention

In the gas-blowing vaporizing and drying device according to the present invention, unlike conventional gas-blowing vaporizing and drying devices, each collection container includes a solution-introducing tube and a gas-introducing tube. As a result, even if the solution-introducing tube and the gas-introducing tube are contaminated by powderization, the contamination does not influence the next collection container, and hence carry-over contamination does not occur. The gas-blowing vaporizing and drying device according to the present invention can be suitably used in a preparative separation-purification system.

BRIEF DESCRIPTION OF THE DRAWINGS

FIG. 8 is a schematic configuration diagram illustrating an automatic sample injecting system to which fixing means of the present invention can be applied.

MODES FOR CARRYING OUT THE INVENTION

First Embodiment

A preparative separation-purification system that is a first embodiment of a gas-blowing vaporizing and drying device according to the present invention is described with reference to FIG. 1 to FIGS. 5A to 5C.

Figure 1:
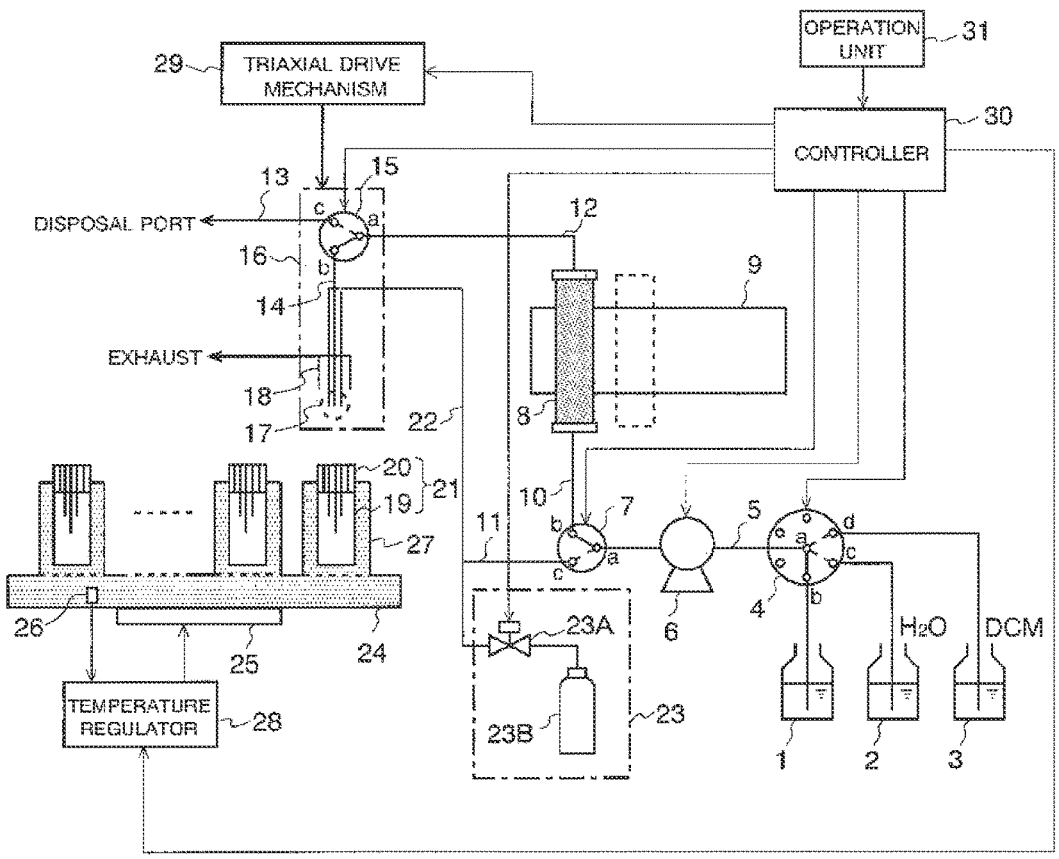
FIG. 1 is a schematic configuration diagram illustrating a preparative separation-purification system that is a first embodiment of a gas-blowing vaporizing and drying device according to the present invention.

FIG. 1 is a schematic configuration diagram of the preparative separation-purification system of the present embodiment. As will be described later, in this preparative separation-purification system, a solution containing a target component is previously fractionated by a preparative liquid chromatograph (not illustrated). It is also possible to change the configuration by directly connecting the preparative liquid chromatograph to the preparative separation-purification system such that a solution fractionated by the preparative liquid chromatograph is directly introduced into the preparative separation-purification system.

In FIG. 1, a solution container 1 houses a previously fractionated solution containing a target component. The solvent of this solution is mainly the mobile phase used in the preparative liquid chromatograph. A pure water container 2 houses pure water ($H_2O$), while an eluting solvent container 3 houses dichloromethane (DCM). A selector valve 4 switches the passage so as to selectively allow one of the three kinds of liquid housed in the containers 1, 2, and 3 to flow into a passage 5. A liquid-sending pump 6 for suctioning and sending the liquid at a predetermined flow rate is provided in the passage 5.

The outlet end of the passage 5 is connected to port a of a selector valve 7. A passage 10 leading to a trap column 8 packed with an adsorbent for capturing the target component is connected to port b of the selector valve 7, and a passage 11 leading to a gas sending passage 22 (which will be described later) is connected to port c of the selector valve 7. The selector valve 7 selectively connects one of the passages 10 and 11 to the passage 5.

The trap column 8 is held in a substantially vertical position by a column rack 9, with the inlet end (to which the passage 10 is to be connected) directed downward and the outlet end (to which a passage 12 is to be connected, as will be described later) directed upward. Although only one trap column 8 is illustrated in FIG. 1, the column rack 9 can hold a plurality of trap columns 8, as indicated by the dotted line in FIG. 1.

The passage 12, with one end connected to the outlet end of the trap column 8, has the other end connected to port a of a selector valve 15, which is incorporated in a fraction collector head (connection unit) 16. A passage 14 is connected to port b of the selector valve 15, and a passage 13 leading to a disposal port is connected to port c of the selector valve 15. The selector valve 15 selectively connects one of the passages 13 and 14 to the passage 12.

Figure 3A:
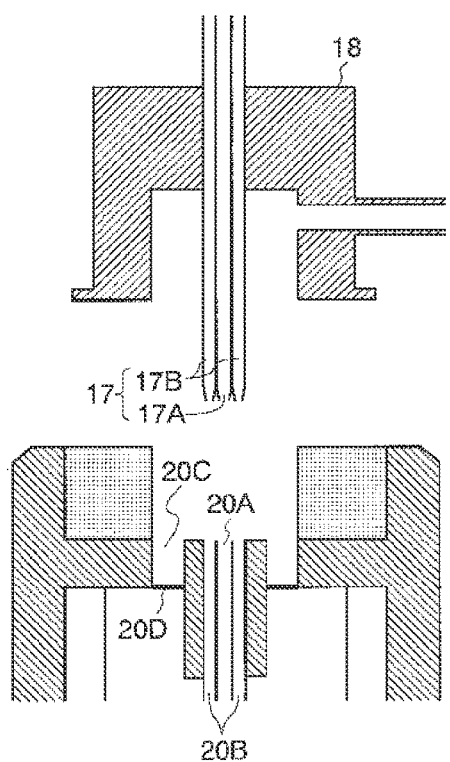
FIGS. 3A and 3B are explanatory views of a gas-blowing vaporizing and drying process performed by the preparative separation-purification system of the present embodiment.

The fraction collector head 16, which is provided with a passage connection portion 17 and an exhaust duct 18, can be moved in both vertical and horizontal directions by a triaxial drive mechanism 29 including a plurality of motors and other components. The passage connection portion 17 has a double-tube structure in which a solution connection tube 17A connected to the passage 14 is an inner tube while a gas connection tube 17B connected to the passage 22 (which will be described later) is an outer tube (FIG. 3A). A gas is sent from a gas supply unit 23, which is provided with a proportional valve 23A, a gas cylinder 23B, and other components, to the gas connection tube 17B through the passage 22.

A container rack 24 is provided with a heater 25, a temperature sensor 26 (e.g. thermistor), and temperature regulated blocks 27. Each collection container 21, which is used for collecting the target component obtained by preparative separation and purification, is individually housed in one of the temperature regulated blocks 27 on the container rack 24. The container rack 24 and the temperature regulated blocks 27 are made of a material with high thermal conductivity, such as aluminum, and the outer surfaces thereof are covered with an insulating material to prevent heat from escaping to the surroundings.

At least the bottom portion of each collection container 21 is in close contact with the temperature regulated block 27 such that the conduction of heat from the temperature regulated block 27 is facilitated. Desirably, the circumferential side surface of the collection container 21 may also be in contact with the temperature regulated block 27. A temperature regulator 28, which is provided apart from the container rack 24, regulates a heating electric current supplied to the heater 25 such that the temperature monitored by the temperature sensor 26 is a target temperature. By this operation, the collection containers 21 are heated to and maintained at an appropriate constant temperature.

Figure 2A:
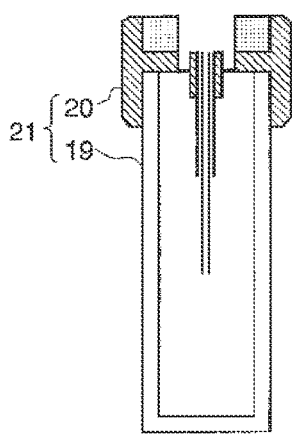
FIGS. 2A and 2B are vertical sectional views of a collection container in the preparative separation-purification system of the present embodiment.
Figure 2B:
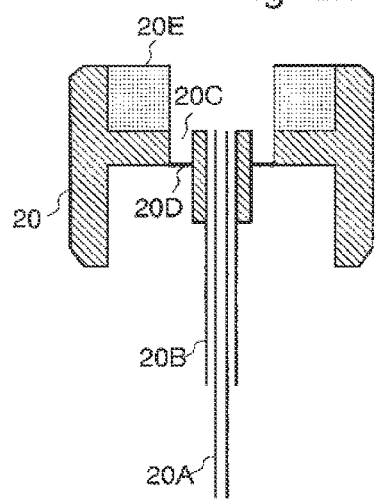

As illustrated in FIG. 1 and FIGS. 2A to 2B, the collection container 21 includes a collection container body 19 and a cap 20 to be fitted to the upper opening of the collection container body 19. As a characteristic structure of the present invention, the cap 20 includes a solution-introducing tube 20A and a gas-introducing tube 20B for respectively introducing the solution and the gas sent from the passage connection portion 17, into the collection container 21. The solution-introducing tube 20A and the gas-introducing tube 20B have a double-tube structure in which the solution-introducing tube 20A is an inner tube while the gas-introducing tube 20B is an outer tube.

The cap 20 further includes an exhaust port 20C. The exhaust port 20C is provided with a filter 20D for preventing a powderized solute from passing therethrough.

Figure 3B:
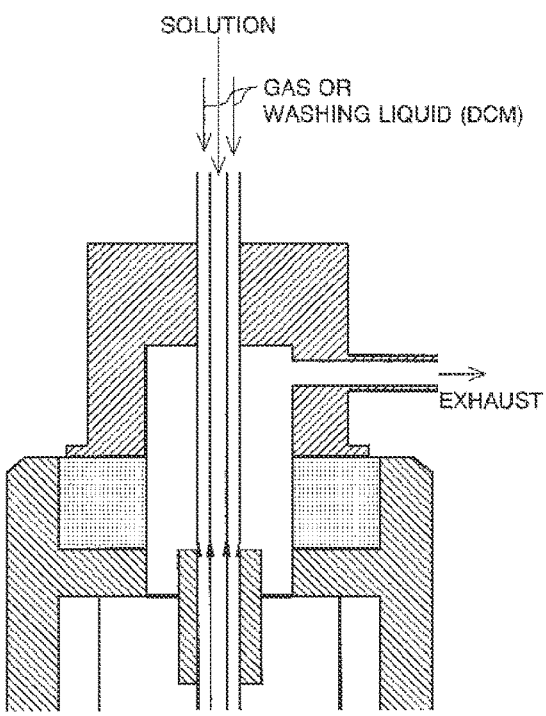

The fraction collector head 16 is moved by the triaxial drive mechanism 29 to a position above any one of the collection containers 21 housed in the container rack 24, and is then moved downward such that the solution connection tube 17A and the gas connection tube 17B of the passage connection portion 17 are respectively connected to the solution-introducing tube 20A and the gas-introducing tube 20B provided to the cap 20 (FIG. 3B). At this time, the exhaust duct 18 is also moved downward, and is brought into close contact with the cap 20 by means of a cushion 20E provided to the cap 20. An exhaust fan (not illustrated) is provided downstream of the exhaust duct 18, whereby the vaporized solvent and other substances in the collection container 21 pass through the exhaust port 20C and the exhaust duct 18, to be discharged to the outside of the collection container 21.

Note that, instead of the fraction collector head 16, the container rack 24 may be moved such that the solution connection tube 17A and the gas connection tube 17B are respectively connected to the solution-introducing tube 20A and the gas-introducing tube 20B.

A controller 30, which includes a CPU and other components, automatically conducts preparative separation-purification work by controlling the switching operations of the selector valves 4, 7, and 15, the operations (flow rate or flow velocity) of the liquid-sending pump 6 and the gas supply unit 23, the setting of the target temperature of the temperature regulator 28, the movement of the fraction collector head 16 through the triaxial drive mechanism 29, and other operations according to a preset program. An operation unit 31 is provided to allow users to enter and set conditions for the preparative separation-purification work as well as other information.

Next, a procedure of the vaporizing and drying process performed by the preparative separation-purification system of FIG. 1 is described. Initially, in order to capture a target component on the adsorbent in the trap column 8, the controller 30 sets the selector valve 4 to connect the solution container 1 (port b) and the passage 5 (port a), and operates the liquid-sending pump 6 to send liquid at a predetermined constant flow rate. The controller 30 further sets the selector valve 7 to connect the passage 5 (port a) and the passage 10 (port b), and sets the selector valve 15 to connect the passage 12 and the passage 13.

The liquid-sending pump 6 suctions the solution from the solution container 1, and introduces the solution into the trap column 8. Consequently, the target component in the solution is captured on the adsorbent in the trap column 8. The mobile phase from which the target component has been removed is discharged into the disposal port through the passages 12 and 13.

After the solution is supplied to the trap column 8 for a predetermined period of time or until the solution prepared in the solution container 1 is completely used, the controller 30 switches the selector valve 4 so as to connect the pure water container 2 (port c) and the passage 5 (port a). Consequently, the liquid-sending pump 6 begins to suction pure water from the pure water container 2 and introduce it into the trap column 8. As a result, unwanted water-soluble substances, such as salt that has attached to the adsorbent during the preceding process of capturing the target component, are removed from the trap column 8. By this supply of pure water, the mobile phase remaining inside of the trap column 8 immediately before the beginning of the supply of pure water is replaced by the water, and the trap column 8 becomes filled with the water. The target component captured on the adsorbent is strongly adsorbed and barely eluted into the water. Hence, at this point, the target component remains in the captured state within the trap column 8.

Subsequently, the controller 30 controls the triaxial drive mechanism 29 to: move the fraction collector head 16 to a position above a previously designated collection container 21; and then move the fraction collector head 16 downward to a predetermined height such that the outlet ends of the solution connection tube 17A and the gas connection tube 17B are respectively fitted to the inlet ends of the solution-introducing tube 20A and the gas-introducing tube 20B (FIG. 3B). Then, the controller 30 switches the selector valve 4 so as to connect the eluting solvent container 3 (port d) and the passage 5 (port a). Consequently, the liquid-sending pump 6 begins to suction dichloromethane from the eluting solvent container 3 and introduce the same into the trap column 8. At this time, the liquid-sending pump 6 is operated at a predetermined liquid-sending flow rate lower than that in the above-mentioned operation of sending the solution or pure water. Further, the controller 30 gives an instruction on the target temperature to the temperature regulator 28, and controls the temperature regulator 28 to begin the heating of the temperature regulated block 27. Thus, the collection container 21 begins to be heated. The target temperature may be, for example, set to be approximately equal to or slightly higher than the boiling point of dichloromethane, e.g. from 40 to 45 degrees Celsius.

The dichloromethane introduced into the trap column 8 is barely mixed with the water existing in the trap column 8, and the interface between the dichloromethane and the water gradually ascends. That is to say, the dichloromethane level gradually rises from the bottom portion of the trap column 8, pushing the water upward. The water thus pushed upward overflows from the upper outlet end of the trap column 8 and flows through the selector valve 15 and the passage 13 to reach the disposal port. Meanwhile, due to the strong eluting power of the dichloromethane, the target component captured in the trap column 8 is eluted into the dichloromethane being accumulated in the trap column 8.

After a predetermined period of time, when the water is completely removed from the trap column 8, the selector valve 15 is switched from the passage 13 (port c) to the passage 14 (port b), and begins the preparative separation of the target component. Further, the controller 30 controls the gas supply unit 23 to begin the supply of nitrogen gas (or another inert gas). The gas sent from the gas supply unit 23 flows through the passage 22 and the gas connection tube 17B into the gas-introducing tube 20B, and begins to be ejected from the tip of the gas-introducing tube 20B. The solution sent from the trap column 8, i.e. the dichloromethane containing the target component, flows through the passages 12 and 14 and the solution connection tube 17A, to be eventually dropped from the tip of the solution-introducing tube 20A. While being dropped, the solution is sheared into fine droplets and scattered around by the gas flow blown at the solution.

The collection container 21 is heated to a temperature as high as the boiling point of dichloromethane by heat conduction from the temperature regulated block 27 with the heater 25 as a heat source. Hence, when the fine droplets of the solution attach to the inner circumferential wall and the inner bottom wall of the collection container 21, the solvent (dichloromethane) in the droplets immediately vaporizes, so that the target component remains in the form of powder. In this way, the target component in the form of powder deposits on the inner circumferential wall and the inner bottom wall of the collection container 21.

After the processes described above are completed, the fraction collector head 16 is moved upward, and is disconnected from the cap 20. If another target component is to be successively powderized, the fraction collector head 16 is moved to the position where the next collection container 21 is set, and the processes are similarly performed.

The procedure of the gas-blowing vaporizing and drying process performed by the preparative separation-purification system of the present embodiment is described hereinabove. In the course of the gas-blowing vaporizing and drying process, the solute may deposit on the tip of the solution-introducing tube 20A, grow along the outer circumference of the solution-introducing tube 20A, and invade even the inside of the gas-introducing tube 20B. In such a case, the gas supply from the gas supply unit 23 is temporarily stopped, and the selector valve 7 is switched from the passage 10 (port b) to the passage 11 (port c). The dichloromethane from the eluting solvent container 3 is now redirected to the passage 11, and hence the dropping of the solution from the trap column 8 into the collection container 21 is also stopped.

The dichloromethane sent to the passage 11 is introduced into the passage 22, and flows through the gas connection tube 17B into the gas-introducing tube 20B. As described above, dichloromethane has a strong eluting power, and hence the deposited substance that has invaded the inside of the gas-introducing tube 20B is dissolved and washed away by the dichloromethane introduced into the gas-introducing tube 20B. After that, the selector valve 7 is switched from the passage 11 (port c) to the passage 10 (port b), and the gas supply from the gas supply unit 23 is resumed, whereby the above-mentioned gas-blowing vaporizing and drying process is continued.

Note that, according to the following method, it is possible to prevent the solute (substance) deposited on the tip of the solution-introducing tube from growing along the outer circumference of the solution-introducing tube 20A and invading the inside of the gas-introducing tube 20B.

As a result of experiments, the inventor of the present invention found out that, because the distance at which the deposited substance grew along the outer circumference of the solution-introducing tube 20A had its limit, the deposited substance did not grow at a given distance or more and that a distance w of this limit substantially depended on the surface tension of the solvent and the contact angle of the solvent to the solution-introducing tube 20A.

The inventor of the present invention carried out the experiments under the following conditions. Polytetrafluoroethylene (PTFE), which is one of fluorine resin materials, was used as the constituent material of the solution-introducing tube 20A. Dichloromethane was used as the solvent. In this case, the contact angle to the solution-introducing tube 20A was 114°. The inner diameter of the solution-introducing tube 20A was set to 0.8 mm, the flow rate of the solution fed to the solution-introducing tube 20A was set to 0.1 mL/min, and the flow rate of the gas fed to the gas-introducing tube 20B was set to 1.6 L/min.

Under the above-mentioned conditions, the growth of the deposited substance was observed. As a result, the deposited substance grew upward at a substantially constant speed for the first 30 minutes, but this growth speed gradually became slower. Eventually, the deposited substance stopped growing after the elapse of 1 hour or more. The growth limit distance w at that time was 9 mm.

Figure 4A:
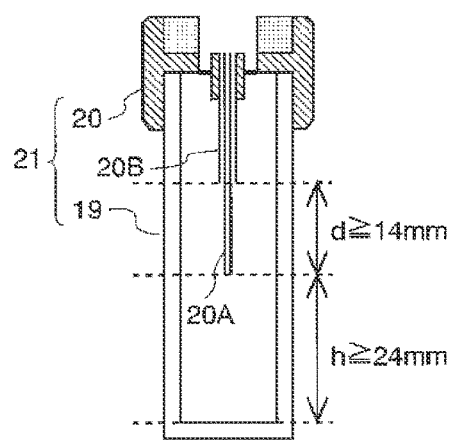
FIGS. 4A to 4D are vertical sectional views of the collection container in the preparative separation-purification system of the present embodiment.

The above experiment results prove that the growth limit distance w significantly depends on the contact angle of the solvent and the surface tension of the solvent (which has a correlation with the contact angle). Under the above-mentioned conditions, if a distance d between the tip of the solution-introducing tube 20A and the tip of the gas-introducing tube 20B is set to be 9 mm or more, the outlet of the gas-introducing tube can be prevented from being clogged with the deposited and grown solute. In the present embodiment, on the safe side, the distance d was set to 14 mm that was about 1.5 times the growth limit distance w confirmed in the experiments (FIG. 4A).

In a case where ethylene tetrafluoroethylene (ETFE) was used as the constituent material of the solution-introducing tube 20A, and dichloromethane was used as the solvent, the contact angle was 96°, and the deposited substance grew up to 12 mm along the outer circumference of the solution-introducing tube 20A.

Thus, it is desirable to appropriately change the distance d between the tip of the solution-introducing tube 20A and the tip of the gas-introducing tube 20B, depending on the used solvent and the used constituent material of the solution-introducing tube 20A.

The deposited substance grows not only upward but also downward along the solution-introducing tube 20A. The deposited substance that grows downward comes off the tip of the solution-introducing tube 20A under its own weight after growing to some degrees. If the distance between the tip of the solution-introducing tube 20A and the bottom portion of the collection container 21 is short, the deposited substance comes into contact with the bottom portion before coming off, and connects the tip of the solution-introducing tube 20A and the bottom portion of the collection container 21 in a columnar shape. If the deposited substance connects the tip of the solution-introducing tube 20A and the bottom portion of the collection container 21 in this way, the column diameter becomes larger with the passage of time. As a result, the tip of the solution-introducing tube 20A is clogged with the deposited substance.

As a result of experiments carried out by the inventor of the present invention, when a distance h between the bottom portion of the collection container 21 and the tip of the solution-introducing tube was 24 mm or more, the deposited substance could be prevented from being formed in such a columnar shape (FIG. 4A).

Figure 4B:
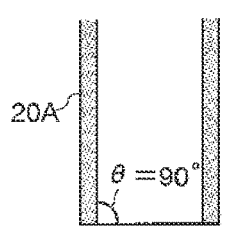
Figure 4C:
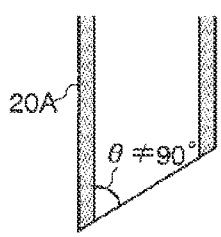

As a result of further experiments carried out by the inventor of the present invention, it was confirmed that, as the cross-sectional area of the outlet end face of the solution-introducing tube 20A was larger, the amount of deposited substance increased. For example, in the case of such a shape as illustrated in FIG. 4C in which the outlet end face is obliquely cut, the cross-sectional area of the outlet end face is larger, and the amount of deposited substance increases. Hence, it is desirable to cut the outlet end face of the solution-introducing tube 20A in the direction perpendicular to the longitudinal direction of the solution-introducing tube 20A such that the cross-sectional area thereof is the smallest (FIG. 4B).

Figure 4D:
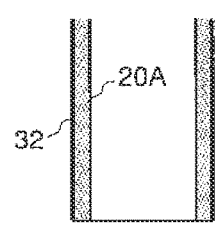

As described above, it is desirable that the solution-introducing tube 20A have a large contact angle on at least its outer circumferential surface. A fluorine resin material, which is an example of such materials having a large contact angle, can be used as the constituent material of the solution-introducing tube 20A. The outer circumferential surface of the solution-introducing tube 20A may be coated with a layer 32 made of a fluorine resin material (FIG. 4D).

Further, in the preparative separation-purification system of the present embodiment, as illustrated in FIG. 5, a screw thread 33A can be provided on the upper outer circumferential surface of the container body 19, and a thread groove 33B corresponding to the screw thread 33A can be provided on the inner circumferential surface of the cap 20 to be fitted to the upper opening of the container body 19. Moreover, a thread groove 34B can be provided on the upper inner circumferential surface of the temperature regulated block 27, and a screw thread 34A corresponding to the thread groove 34B can be provided on the outer circumferential surface of the cap 20. These screw threads and thread grooves serve as fixing means for fixing the collection container 21 to the temperature regulated block 27. Hereinafter, a pair of the screw thread 33A and the thread groove 33B is referred to as a first screw 33, and a pair of the screw thread 34A and the thread groove 34B is referred to as a second screw 34.

The cap 3520 is put on the container body 19, and the cap 20 is turned. Consequently, the cap 20 is fixed to the container body 19 by the first screw 33, and is fitted to the upper opening of the container body 19. This is a structure that has frequently been adopted up to now.

Meanwhile, in the structure of FIG. 5, for example, the container body 19 to which the cap 20 is fitted by the first screw 33, is inserted into the temperature regulated block 27, and the cap 20 is turned together with the entire collection container 21, whereby the cap 20 and the temperature regulated block 27 are fixed to each other by the second screw 34. Because the temperature regulated block 27 is part of the container rack 24, the weight of the entire container rack 24 prevents the collection container 21 from being lifted up together with the cap 20 when the fraction collector head 16 is moved upward.

Figure 5A:
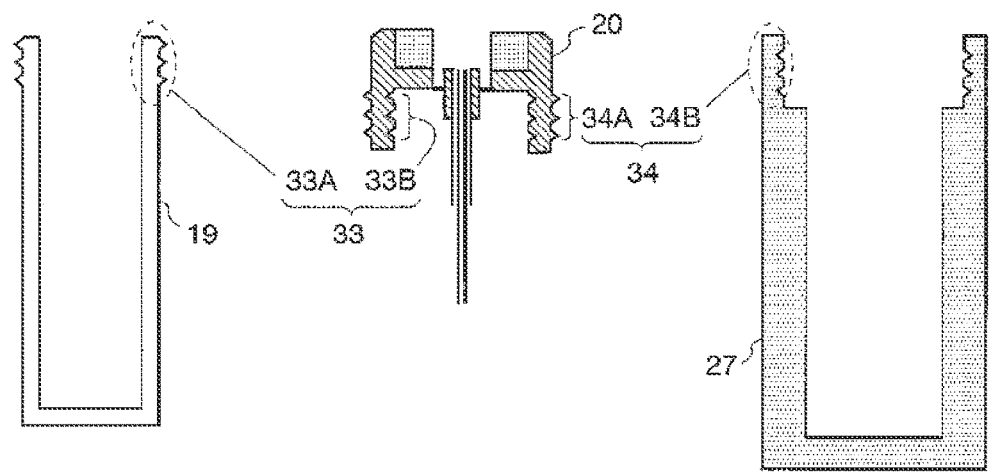
FIGS. 5A to 5C are vertical sectional views of the vicinity of the collection container in the preparative separation-purification system of the present embodiment.
Figure 5B:
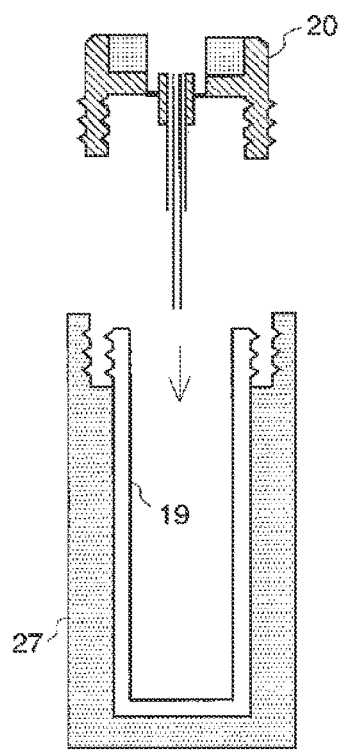
Figure 5C:
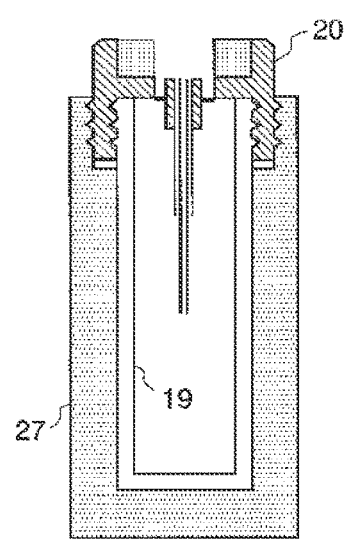

Note that it is desirable that the axes and turn directions of the first screw 33 and the second screw 34 be the same as each other. With this configuration, the collection container 21 can be fixed to the temperature regulated block 27 according to the procedure illustrated in FIGS. 5A to 5C. FIG. 5A illustrates the state where all the container body 19, the cap 20, and the temperature regulated block 27 are not fitted or inserted. First, as illustrated in FIG. 5B, the container body 19 is housed in the temperature regulated block 27. At this point, the container body 19 is not fixed to the temperature regulated block 27. Subsequently, as illustrated in FIG. 5C, the cap 20 is put on the upper opening of the container body 19, and is turned. Consequently, the cap 20 is fixed by the first screw 33, and simultaneously, the cap 20 and the temperature regulated block 27 are fixed to each other by the second screw 34.

In this way, if the screw axes and turn directions of the first screw 33 and the second screw 34 are the same as each other, both the pair of the cap 20 and the container body 19 and the pair of the cap 20 and the temperature regulated block 27 can be fixed simultaneously.

In the case where any one or both of the axes and turn directions of the first screw 33 and the second screw 34 are different from each other, the cap 20 is fitted to the container body 19, and the container body 19 is then inserted into the temperature regulated block 27. In this state, the cap 20 is turned together with the entire collection container 21, whereby the cap 20 and the temperature regulated block 27 may be fixed to each other by the second screw 34. As a matter of course, also in the example of FIGS. 5A to 5C, the fixing by the first screw 33 and the fixing by the second screw 34 can be performed independently.

Note that fixing means for fixing the cap 20 and the temperature regulated block 27 is not limited to the screws, and may be fixed by any other means such as an engaging lock. Further, instead of indirectly fixing the collection container 21 and the container rack 24 with the intermediation of the cap 20, the collection container 21 and the container rack 24 may be directly fixed to each other.

Second Embodiment

Figure 6:
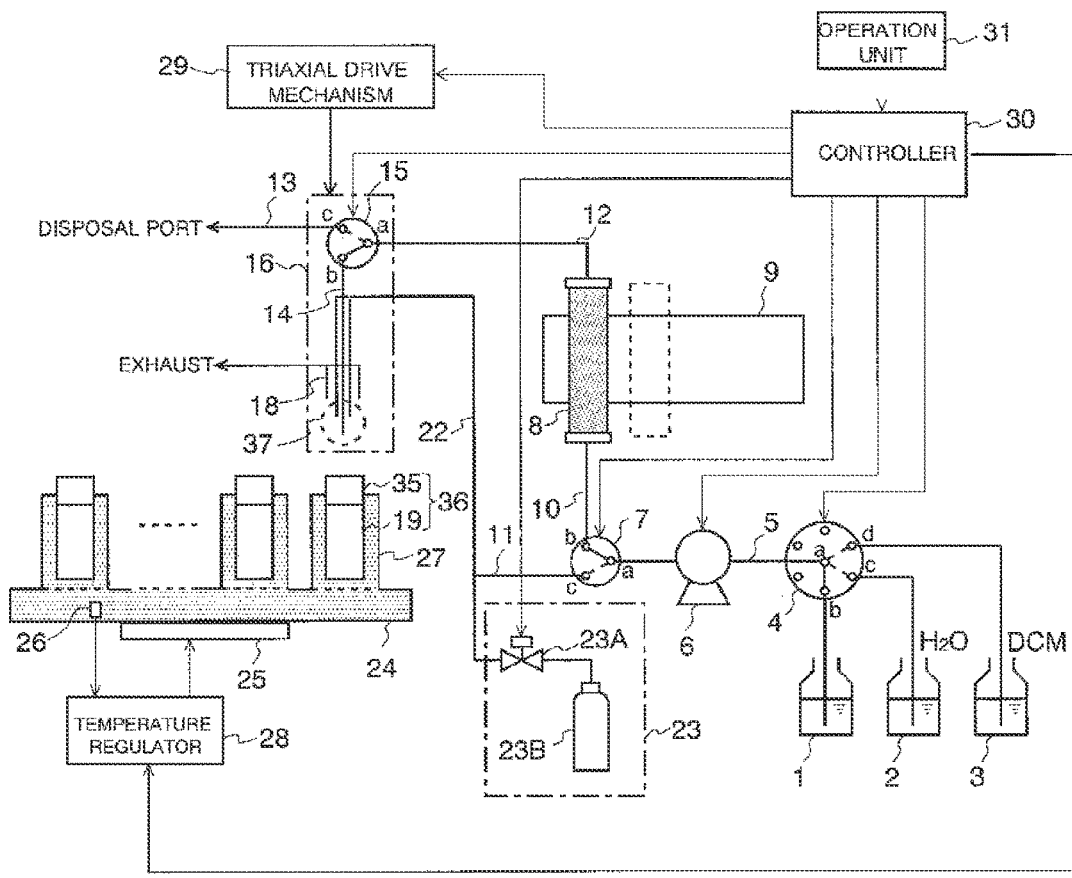
FIG. 6 is a schematic configuration diagram illustrating a preparative separation-purification system that is a second embodiment of the gas-blowing vaporizing and drying device according to the present invention.

The above-mentioned fixing means can also be applied to a conventional preparative separation-purification system using a needle. FIG. 6 is a schematic configuration diagram of a preparative separation-purification system of a second embodiment. This preparative separation-purification system is different from the preparative separation-purification system of the first embodiment illustrated in FIG. 1 in that a cap 35 does not include the solution-introducing tube 20A, the gas-introducing tube 20B, the exhaust port 20C, and the filter 20D and that a needle 37 having a double-tube structure of a solution-introducing tube and a gas-introducing tube is used. Note that, with regard to the needle 37 of the present embodiment, when the gas-introducing tube provided to the needle 37 is washed, a washing liquid is supplied through the passage 22 for gas supply, according to a procedure similar to that in the first embodiment. As a result, even if a deposited substance invades the inside of the gas-introducing tube, the deposited substance can be washed away.

Figure 7A:
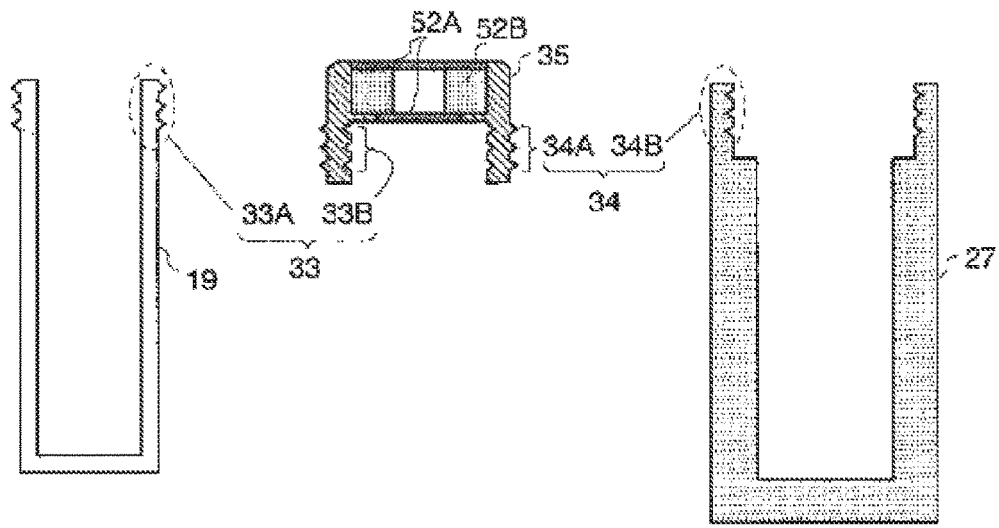
FIGS. 7A to 7C are vertical sectional views of the vicinity of a collection container in the preparative separation-purification system of the present embodiment.
Figure 7B:
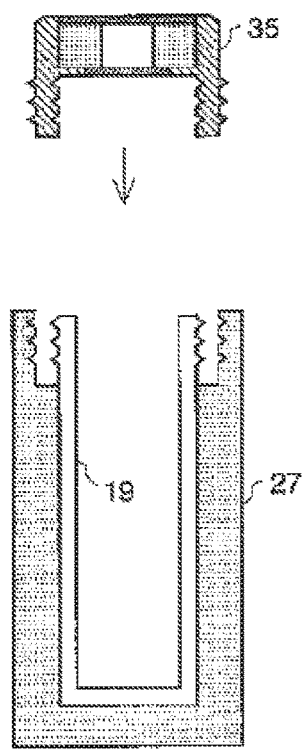
Figure 7C:
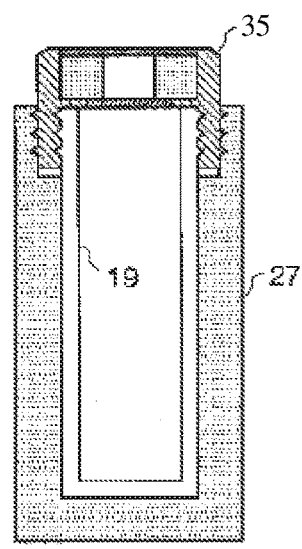
Figure 9A:
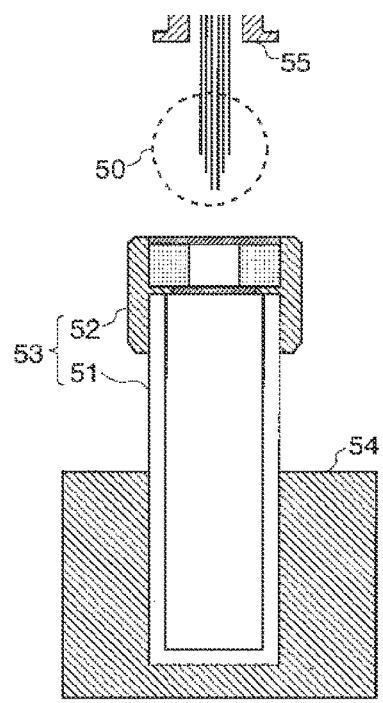
FIGS. 9A to 9D are explanatory views of a conventional gas-blowing vaporizing and drying process.
Figure 9B:
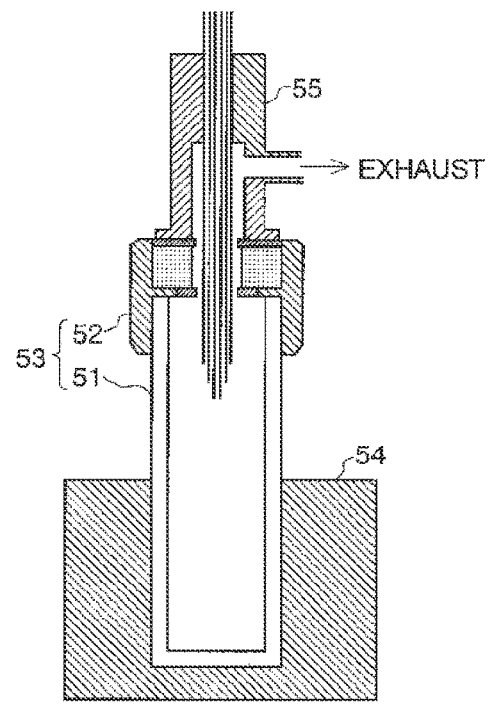
Figure 9C:
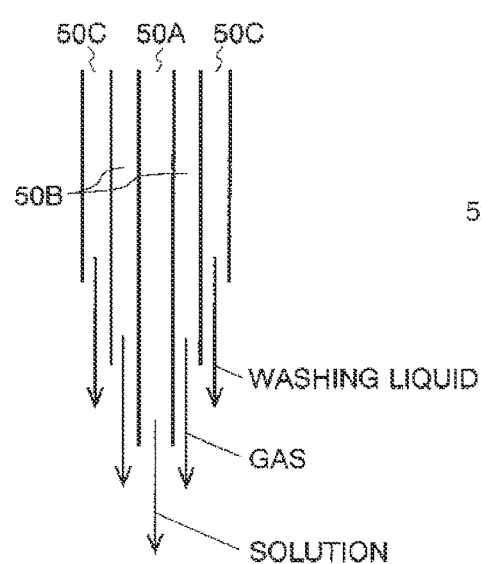
Figure 9D:
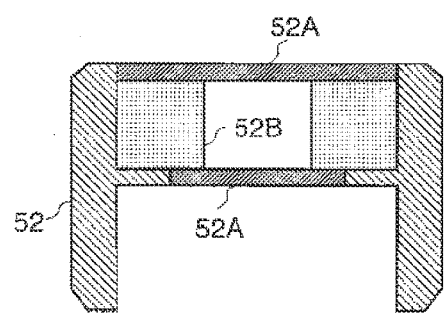

In the preparative separation-purification system of the present embodiment, during the gas-blowing vaporizing and drying process, the needle 37 penetrates through two septa 52A of the cap 35 illustrated in FIGS. 7A to 7C, and the tip thereof is inserted into a collection container 36. Then, when the gas-blowing vaporizing and drying process is ended, the fraction collector head 16 is moved upward together with the needle 37, and the needle 37 is pulled out of the cap 35. When the fraction collector head 16 is moved upward, the collection container 36 may be lifted up from the temperature regulated block 27 by the frictional force that acts between the needle 37 and the septa 52A. In order to prevent this, similarly to the fixing means illustrated in FIGS. 5A to 5C the cap 35 and the temperature regulated block 27 can be provided with the second screw 34 including the screw thread 34A and the thread groove 34B. A procedure for fixing the cap 35 to the temperature regulated block 27 is the same as that illustrated in FIG. 5. In this way, the cap 35 and the temperature regulated block 27 are fixed to each other, whereby the collection container 36 and the temperature regulated block 27 are fixed to each other through the cap 35. Hence, also in the conventional preparative separation-purification system, the collection container 36 can be prevented from being lifted up from the temperature regulated block 27 (container rack 24) when the needle 37 is pulled out of the collection container 36.

The fixing means can be applied to not only the preparative separation-purification system but also such an automatic sample injecting system as illustrated in FIG. 8. Also in the automatic sample injecting system, in order to collect a sample enclosed in a sample container 43, a needle 41 is stuck through a cap 44 with septa, and the needle 41 is pulled out of the cap 44 after the sample collection. Accordingly, if a container rack 42, the sample container 43, and the cap 44 are fixed to each other using fixing means similar to that illustrated in FIG. 7, the sample container 43 can be prevented from being lifted up from the container rack 42 when the needle 41 is pulled out.

EXPLANATION OF NUMERALS

1 . . . Solution Container
2 . . . Pure Water Container
3 . . . Eluting Solvent Container
4 . . . Selector Valve
5, 10, 11, 12, 13, 14, 22 . . . Passage
6 . . . Liquid-Sending Pump
7 . . . Selector Valve
8 . . . Trap Column
9 . . . Column Rack
15 . . . Selector Valve
16 . . . Fraction Collector Head
17 . . . Passage Connection Portion
17A . . . Solution Connection Tube 17B . . . Gas Connection Tube
18, 55 . . . Exhaust Duct
19, 51 . . . Collection Container Body
20, 35, 44, 52 . . . Cap
20A, 50A . . . Solution-Introducing Tube
20B, 50B . . . Gas-Introducing Tube
20C . . . Exhaust Port
20D . . . Filter
20E, 52B . . . Cushion
21, 36, 53 . . . Collection Container
23 . . . Gas Supply Unit
23A . . . Proportional Valve
23B . . . Gas Cylinder
24, 42 . . . Container Rack
25 . . . Heater
26 . . . Temperature Sensor
27, 54 . . . Temperature Regulated Block
28 . . . Temperature Regulator
29 . . . Triaxial Drive Mechanism
30 . . . Controller
31 . . . Operation Unit
32 . . . Layer
33 . . . First Screw
33A, 34A . . . Screw Thread
33B, 34B . . . Thread Groove
34 . . . Second Screw
37, 41, 50 . . . Needle
43 . . . Sample Container
50C . . . Washing-Liquid-Introducing Tube
52A . . . Septum

The invention claimed is:

1. A gas-blowing vaporizing and drying device, comprising:
a collection container for collecting a target component; and
a collector head for supplying gas and a solution containing the target component into the collection container, the gas-blowing vaporizing and drying device being for blowing the gas at the solution, and thus nebulizing the solution to promote vaporization of a solvent while dropping the solution into the collection container, in which
the collector head includes:
a solution connection tube through which the solution flows; and
a gas connection tube through which the gas flows;
the collection container includes:
a collection container body;
a lid including:
a solution-introducing tube being attachable to and detachable from the solution connection tube and being fixed to the lid, and an inlet end of the solution-introducing tube protrudes from the collection container to be connected to an outlet end of the solution connection tube; and
a gas-introducing tube being attachable to and detachable from the gas connection tube and being fixed to the lid, and an inlet end of the gas-introducing tube protrudes from the collection container to be connected to an outlet end of the gas connection tube; and
an exhaust port; and
a collector head drive mechanism for connecting or disconnecting the solution connection tube and the solution-introducing tube, and for connecting or disconnecting the gas connection tube and the gas-introducing tube, by vertically moving the collector head.

2. The gas-blowing vaporizing and drying device according to claim 1, wherein the exhaust port includes a filter.

3. The gas-blowing vaporizing and drying device according to claim 1, further comprising:
gas-introducing tube washing means including:
a passage connected to a gas passage for introducing the gas into the gas connecting tube in a middle thereof; and
a liquid-sending pump for feeding a washing liquid to the gas-introducing tube through the passage and the gas passage.

4. The gas-blowing vaporizing and drying device according to claim 1, wherein
the solution-introducing tube and the gas-introducing tube have a double-tube structure in which the solution-introducing tube is an inner tube while the gas-introducing tube is an outer tube, and
an outlet end of the solution-introducing tube protrudes from an outlet end of the gas-introducing tube.

5. The gas-blowing vaporizing and drying device according to claim 4, wherein a distance between an outlet end of the solution-introducing tube and an outlet end of the gas-introducing tube is 1.5 times or more a given distance at which a deposited substance of the solution grows along an outer circumferential surface of the solution-introducing tube from the outlet end of the solution-introducing tube, the given distance being assumed based on surface tension of the solvent and a contact angle of the solvent to the outer circumferential surface of the solution-introducing tube.

6. The gas-blowing vaporizing and drying device according to claim 1, wherein the solution-introducing tube is made of a fluorine resin material.

7. The gas-blowing vaporizing and drying device according to claim 1, wherein an end face of the outlet end of the solution-introducing tube is orthogonal to an axis of the solution-introducing tube.

8. The gas-blowing vaporizing and drying device according to claim 1, further comprising:
a housing unit for housing the collection container, the housing unit being fixed at a predetermined position; and
fixing means for fixing the collection container to the housing unit, the fixing means being provided to any one or both of the collection container and the housing unit.

9. The gas-blowing vaporizing and drying device according to claim 8, wherein
an outer circumferential surface of the lid and an inner circumferential surface of the housing unit include a screw thread and a thread groove corresponding to each other,
an inner circumferential surface of the lid and an outer circumferential surface of the collection container body include a screw thread and a thread groove corresponding to each other, and
axes and turn directions of a screw pair for fixing the lid and the collection container body and a screw pair for fixing the lid and the housing unit are the same as each other.

* * * * *